United States Patent
Jennings et al.

(10) Patent No.: US 9,623,183 B2
(45) Date of Patent: Apr. 18, 2017

(54) REUSABLE ENGINE FOR AN AUTO-INJECTOR

(75) Inventors: Douglas Jennings, Herts (GB);
Thomas Kemp, Ashwell (GB);
Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1005 days.

(21) Appl. No.: 13/876,167

(22) PCT Filed: Oct. 6, 2011

(86) PCT No.: PCT/EP2011/067499
§ 371 (c)(1),
(2), (4) Date: Jul. 11, 2013

(87) PCT Pub. No.: WO2012/045836
PCT Pub. Date: Apr. 12, 2012

(65) Prior Publication Data
US 2013/0281927 A1    Oct. 24, 2013

Related U.S. Application Data

(60) Provisional application No. 61/432,258, filed on Jan. 13, 2011.

(30) Foreign Application Priority Data

Oct. 8, 2010    (EP) .................................... 10187002

(51) Int. Cl.
*A61M 5/20*    (2006.01)
*A61M 5/32*    (2006.01)
*A61M 5/46*    (2006.01)

(52) U.S. Cl.
CPC ......... *A61M 5/2053* (2013.01); *A61M 5/3204* (2013.01); *A61M 5/326* (2013.01);
(Continued)

(58) Field of Classification Search
CPC .............. A61M 5/2053; A61M 5/3204; A61M 2005/206; A61M 5/46; A61M 5/326; A61M 2005/208
See application file for complete search history.

(56) References Cited

U.S. PATENT DOCUMENTS 5,709,662 A    1/1998    Olive et al.
6,135,979 A *  10/2000   Weston ............... A61M 5/2033
                                                    604/134
(Continued)

FOREIGN PATENT DOCUMENTS

JP    1998113387    5/1998
JP    2005/514082   5/2005
(Continued)

OTHER PUBLICATIONS

International Preliminary Report on Patentability in International Application No. PCT/EP2011/067499, dated Apr. 9, 2013, 4 pages.
(Continued)

*Primary Examiner* — Imani Hayman
*Assistant Examiner* — Hamza Darb
(74) *Attorney, Agent, or Firm* — Fish & Richardson P.C.

(57) ABSTRACT

An engine for an-auto injector for administering a dose of a liquid medicament includes a case arranged to be attached to a package syringe containing a syringe. The case contains a drive capable of, upon activation, pushing the needle from a covered position into an exposed position, and operating the syringe to supply the dose of medicament. The case contains a trigger arranged to lock the drive in a loaded state prior to manual operation and capable of, upon manual operation, releasing the drive for injections. The drive is arranged as a gas spring including a cylinder and a piston with a plunger for transmitting the spring force. A latch is arranged for preventing translating between the cylinder and the case. The latch is disengageable by the released gas spring being
(Continued)

at least nearly fully extended thus allowing the extended gas spring to be translated in a distal direction.

20 Claims, 5 Drawing Sheets

(52) U.S. Cl.
CPC ......... *A61M 5/46* (2013.01); *A61M 2005/206* (2013.01); *A61M 2005/208* (2013.01)

(56) References Cited

U.S. PATENT DOCUMENTS

| | | | |
|---|---|---|---|
| 6,406,455 B1* | 6/2002 | Willis | A61M 5/30 |
| | | | 604/191 |
| 2002/0095120 A1 | 7/2002 | Larsen et al. | |
| 2003/0233070 A1* | 12/2003 | De La Serna | A61M 5/2053 |
| | | | 604/141 |

FOREIGN PATENT DOCUMENTS

| | | |
|---|---|---|
| WO | 03039634 A1 | 5/2003 |
| WO | 2009086250 A1 | 7/2009 |
| WO | 2010057473 A2 | 5/2010 |

OTHER PUBLICATIONS

International Search Report and Written Opinion in International Application No. PCT/EP2011/067499, mailed Apr. 5, 2012, 6 pages.
Rote Liste, "50. Hypophysen-, Hypothalamushormone, andere regulatorische Peptide u. ihre Hemmstoffe," Chapter 50, ed. 2008, 20 pages.

* cited by examiner

REUSABLE ENGINE FOR AN AUTO-INJECTOR

CROSS REFERENCE TO RELATED APPLICATIONS

The present application is a U.S. National Phase Application pursuant to 35 U.S.C. §371 of International Application No. PCT/EP2011/067499 filed Oct. 6, 2011, which claims priority to European Patent Application No. 10187002.0 filed Oct. 8, 2010 and U.S. Provisional Patent Application No. 61/432,258 filed Jan. 13, 2011. The entire disclosure contents of these applications are herewith incorporated by reference into the present application.

FIELD OF INVENTION

The invention relates to a reusable engine for an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide a novel reusable engine for an auto-injector.

The object is achieved by an engine for an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

According to the invention an engine for an auto-injector for administering a dose of a liquid medicament comprises a case having a distal end and a proximal end arranged to be attached to a packaged syringe. The packaged syringe contains a syringe with a hollow needle and a stopper for sealing the syringe and displacing the medicament. The syringe is slidably arranged with respect to the case. The case of the engine contains:

drive means capable of, upon activation:
  pushing the needle from a covered position into an exposed position, and
  operating the syringe to supply the dose of medicament, and
activating means arranged to lock the drive means in a loaded state prior to manual operation and capable of, upon manual operation, releasing the drive means for injection.

According to the invention the drive means is arranged as a gas spring comprising a cylinder and a piston with a plunger for transmitting the spring force. A compressed gas is provided in a high pressure cavity defined between the piston and a distal end of the cylinder. The cylinder is slidably arranged in the case but may be prevented from translation by a latch arranged to lock the cylinder to the case. The latch is disengageable by the released drive means being at least nearly fully extended in a manner to allow the cylinder and thus the whole extended gas spring to be translated in distal direction, e.g. into a clearance provided in the distal end of the case. The drive means, i.e. the gas spring is nearly fully extended at the end of an injection stroke when the medicament has been at least nearly entirely injected into an injection site, e.g. a patient's skin. When the user removes the auto-injector from the injection site it is desirable to hide the needle in order to prevent needle stick injuries. One way to achieve needle safety is to retract the needle into a case or sleeve. Disengaging the cylinder from the case allows the plunger to be moved in distal direction so it does no longer push against the stopper thus allowing the syringe and the needle to be retracted.

The advantage of using a gas spring is that it allows for smaller and more compact engines than conventional compression spring engines. Furthermore a gas spring may be designed with inherent damping so shock loads onto the syringe and stopper may be avoided. A gas spring also has the advantage of less change in force as it expands, compared to a normal compression spring. This means less change in injection rate throughout the dose.

Preferably a cylinder spring may be arranged in the case for biasing the cylinder against the case in distal direction. This allows for actively translating the cylinder in distal direction as soon as the latch has been disengaged. Another mechanism in the packaged syringe, for retracting the syringe and needle in the packaged syringe e.g. a syringe spring can therefore be dimensioned to do just that without having to translate the gas spring.

The compressed gas used in the gas spring may be Nitrogen. Other gases, such as carbon dioxide may also be applied.

The compressed gas may exhibit a pressure of approximately 10 bar when the gas spring is in the loaded state. The gas may also have another pressure remarkably greater than the atmospheric pressure.

In a preferred embodiment the activation means may be arranged as a trigger button laterally arranged at the case. The trigger button may have a dog for engaging the plunger prior to manual operation in a manner to prevent translation of the plunger. The dog is arranged to disengage from the plunger upon manual operation so the plunger may translate in proximal direction forced by the expanding gas.

In an alternative embodiment the trigger button may be arranged at the distal end of the engine, the opposite end to where the needle appears. However, this increases the risk of operating the auto-injector in the wrong direction and subsequent injury by inserting the needle into the user's thumb.

Application of a lateral or side button helps to eliminate that risk.

The dog may be shaped as a loop with an aperture for the plunger. The aperture comprises a narrow portion aligned with the plunger prior to manual operation of the trigger button and a wide portion aligned with the plunger upon manual operation, i.e. pushing the trigger button radially inwards with respect to a longitudinal axis of the engine. The plunger has a main section adjacent to the piston and a locking section proximally from the main section. When the gas spring is in the loaded state the main section is essentially hidden in the cylinder while the locking section is outside the cylinder. The narrow portion of the aperture has a diameter smaller than a diameter of the main section but wider than a diameter of the locking section thus allowing to hold the locking section while preventing the main section from passing through prior to manual operation of the trigger button. The wide portion of the aperture has a diameter at least as wide as the diameter of the main section in order to allow it to pass through when the trigger button has been pressed.

Syringe retraction is ideally triggered when the syringe has been emptied. Due to tolerances in manufacturing of the syringe and other components the exact position of the stopper in relation to the syringe in this situation can differ between different syringes. This may lead to situations where retraction is triggered before the stopper has bottomed out so the syringe is not fully emptied. In other cases the stopper may bottom out before refraction is triggered resulting in the auto-injector stalling and not retracting the syringe at all.

In order to solve both problems, reliably triggering retraction and emptying the syringe, the plunger may be telescoped with a plunger front part, wherein a plunger spring biases the plunger front part against the plunger rear part. The plunger may comprise a shoulder beyond the locking section in proximal direction. The shoulder is followed by a pin, wherein the shoulder has a greater diameter than the pin.

The plunger front part is telescoped with the pin. The plunger spring is arranged on the pin in a manner to bias the plunger front against the shoulder. Alternatively, the pin may be arranged at the plunger front part telescoped with a corresponding bore in the plunger. The plunger spring is defined to generate a force greater than the hydraulic force of the emptying the syringe yet weaker than the force of the gas spring. This allows for pushing the stopper until it bottoms out in the syringe so the syringe is emptied. The gas spring continues pushing the plunger in proximal direction thus partially compressing the plunger spring. The retraction is then triggered as soon as the gas spring is expanded so far as to disengage the latch.

Thus both problems are solved, reliably retracting the hollow needle to a safe position and fully emptying the syringe which is particularly desirable with expensive drugs. Emptying the syringe is also important for dosage accuracy.

In a preferred embodiment a button latch may be arranged in the case, the button latch slidable between a locking position obstructing the trigger button in a manner to prevent it from being pressed and an unlocked position, where the trigger button is allowed to be pressed inwardly. Inadvertently triggering an injection is thus less likely since the button latch has to be operated before the trigger button can be pressed.

The button latch may be arranged to be pushed into the unlocked position by a transfer sleeve arranged in the packaged syringe when a proximal end of the transfer sleeve is pushed against an injection site. The user is thus required to observe a sequence of operation. First, the auto-injector has to be pressed against the injection site. Then the trigger button may be pressed to start the injection.

A valve may be arranged in the cylinder in a manner to restrict venting of a low pressure side of the piston opposite the high pressure cavity. This may be used to specify the damping characteristics of the gas spring so a speed of insertion and injection may be controlled.

Preferably, the valve is defined to ensure a damping rate greater than a damping force generated due to friction between the stopper and an inner wall of the syringe and due to hydraulic resistance of the liquid medicament forced through the hollow needle by the advancing stopper. Since the force on the piston from the compressed gas is always distributed between the damping force of the valve and any load applied to the proximal end of the plunger, the syringe and needle may be advanced in a manner avoiding or minimizing wet injection, i.e. i.e. the liquid medicament is not leaking out of the hollow needle before or during needle insertion.

The reusable engine is preferably used in an auto-injector for administering a dose of a liquid medicament, the auto-injector comprising the engine and the packaged syringe. The syringe is at least partially arranged inside a tubular syringe retainer arranged for connecting the packaged syringe to the engine and for restricting longitudinal motion of the syringe. The syringe and the needle are arranged to be hidden inside the packaged syringe when the drive means is in its loaded state. The syringe is biased in distal direction by a syringe spring and movable in proximal direction by the drive means of the engine into a position with the needle protruding beyond a proximal end of the packaged syringe. The syringe spring serves for retracting the syringe and the needle after the end of the injection provided the plunger has stopped pushing against the stopper and can be translated in distal direction or is actively pulled in distal direction.

A tubular transfer sleeve may be arranged around the syringe in a manner to hide the syringe and the needle when the drive means is in its loaded state. The transfer sleeve is preferably movable in distal direction by a small distance and biased in proximal direction by at least one resilient member. The transfer sleeve extends through the syringe retainer in a manner to engage the button latch of the engine thus providing skin interlock functionality, i.e. the trigger button is prevented from being pressed as long as the transfer sleeve is not translated back by pushing it against the injection site.

A removable cap may be arranged on the packaged syringe for protecting the syringe during shipping and handling and for protecting the user when the packaged syringe is being attached to the engine.

Usually the hollow needle is equipped with a protective needle sheath for keeping the needle sterile and preventing it from being mechanically damaged. The protective needle sheath is attached to the needle when the syringe is assembled.

The cap may be arranged to grip the protective needle sheath. When the cap is removed from the housing in preparation of an injection the protective needle sheath is reliably removed without exposing the user to too high a risk to injure themselves.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The syringe may consist of any rigid material, such as glass or plastics.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
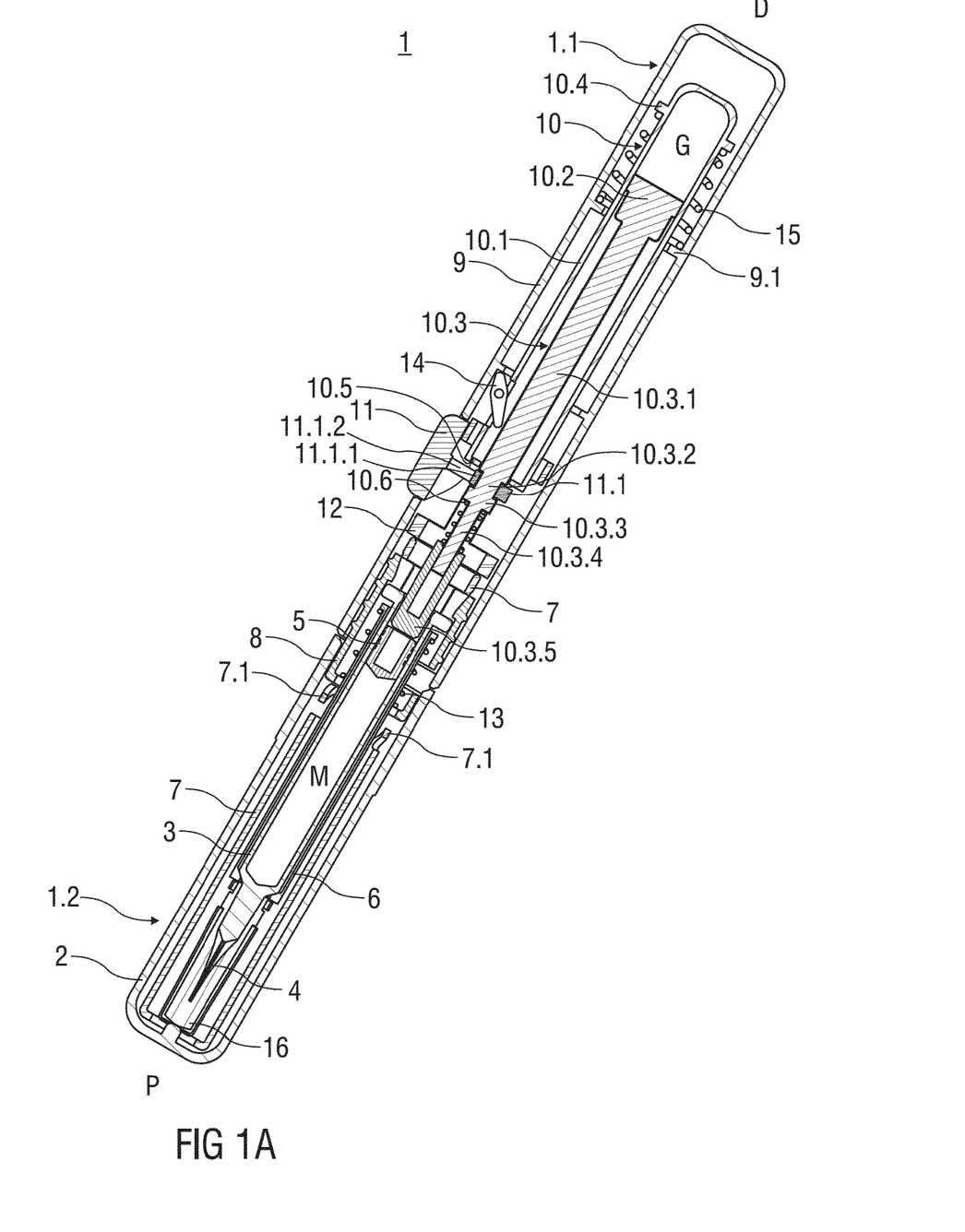
FIG. 1A, and FIG. 1B shows two longitudinal sections of an auto-injector with a gas spring in two different section planes.
Figure 1B:
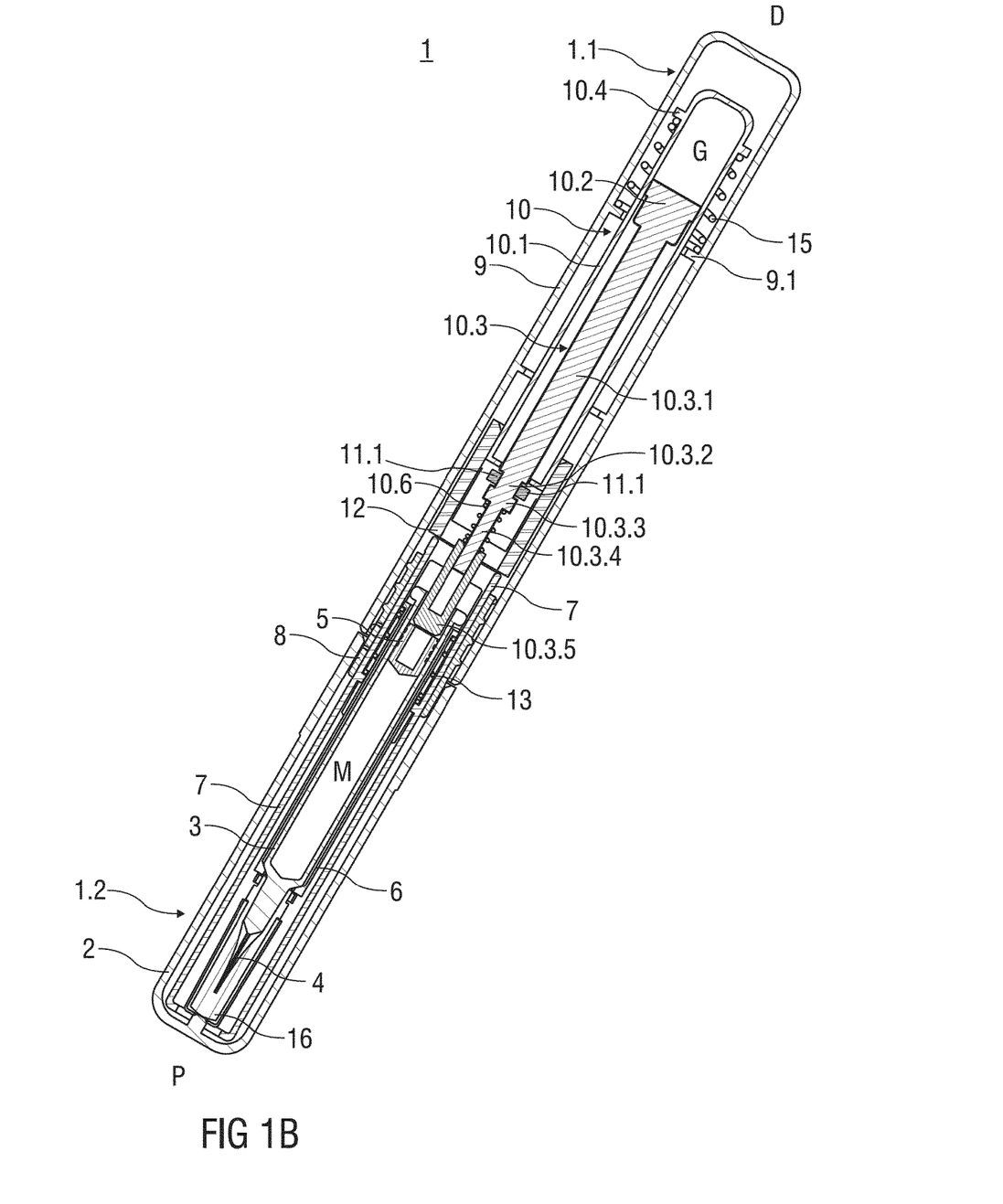

FIG. 1 shows an auto-injector 1. The auto-injector 1 comprises a reusable engine 1.1 and a disposable packaged syringe 1.2.

The disposable packaged syringe 1.2 comprises a cap 2, a syringe 3 with a hollow injection needle 4 and a stopper 5 for sealing the syringe 3 and displacing a liquid medicament M. The syringe 3 is arranged inside a support sleeve 6 which in turn is arranged inside a tubular transfer sleeve 7 which may be translated within a tubular syringe retainer 8. The syringe retainer 8 is arranged to restrict longitudinal translation of the syringe 3.

The reusable engine 1.1 comprises a case 9 with an open proximal end. A gas spring 10 is arranged in the case 9, the gas spring 10 comprising a cylinder 10.1 with a closed distal end and a piston 10.2 arranged to reciprocate in the cylinder 10.1 and seal against the cylinder walls. A high pressure cavity filled with a compressed gas G is defined between the distal end of the cylinder 10.1 and the piston 10.2. The gas G may be Nitrogen at a pressure of approximately 10 bar when the gas spring 10 is in a loaded or compressed state. The piston 10.2 is arranged at a distal end of a plunger 10.3. The cylinder 10.1 may be translated in longitudinal direction in the case 9. A latch 14 is provided for preventing this longitudinal motion by locking the cylinder 10.1 to the case 9. A flexible diaphragm (not illustrated) may be arranged in the cylinder 10.1 under the latch 14 for sealing the cylinder 10.1. A cylinder spring 15, arranged between an internal shoulder 9.1 in the case 9 and an external shoulder 10.4 at the cylinder biases the cylinder 10.1 in distal direction D with respect to the case 9. The cylinder spring 15 is compressed in an initial state of the auto-injector 1. The plunger 10.3 extends in proximal direction P in a manner to allow it to push against the stopper 5 of the syringe 3 when the packaged syringe 1.2 is attached to the reusable engine 1.1.

A trigger button 11 is arranged in a lateral aperture in the case 9. Inside the case 9 a button latch 12 is slidably arranged. It may be slid between a locking position obstructing the trigger button 11 in a manner to prevent it from being pressed and an unlocked position allowing the trigger button 11 to be pressed inwardly.

The trigger button 11 has a dog 11.1 arranged inwardly. The dog 11.1 has as an aperture for the plunger 10.3, the aperture comprising a narrow portion 11.1.1 and a wide portion 11.1.2. The narrow portion 11.1.1 has a diameter smaller than a diameter of a main section 10.3.1 of the plunger 10.3 but wider than the diameter of a locking section 10.3.2 of the plunger 10.3. When the gas spring 10 is in its compressed state, the locking section 10.3.2 is right outside the proximal end of the cylinder 10.1. As long as the trigger button 11 is not pressed the locking section 10.3.2 is held in the narrow portion 11.1.1 of the aperture. The main section 10.3.1 is thicker than the narrow portion 11.1.1 so the gas spring 10 is locked. When the trigger button 11 is being depressed the wide portion 11.1.2 becomes aligned with the plunger 10.3, thus allowing the main section 10.3.1 to pass through the aperture and the gas spring 10 to expand.

Beyond the locking section 10.3.2 in proximal direction P, the plunger 10.3 comprises a shoulder 10.3.3 followed by a pin 10.3.4 with the shoulder 10.3.3 having a greater diameter than the pin 10.3.4. A plunger front part 10.3.5 is telescoped with the pin 10.3.4. A plunger spring 10.6 is arranged on the pin 10.3.4 in a manner to bias the plunger front part 10.3.5 against the shoulder 10.3.3 and the rest of the plunger 10.3.

A valve 10.5 is arranged in or near a proximal face of the cylinder 10.1.

Figure 3:
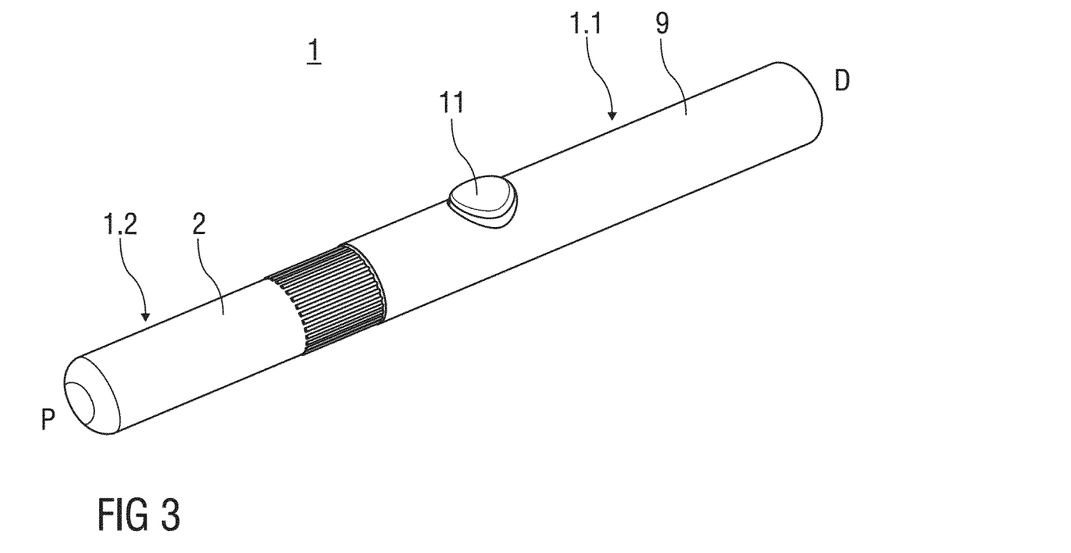
FIG. 3 is an isometric view of the auto-injector.
Figure 4:
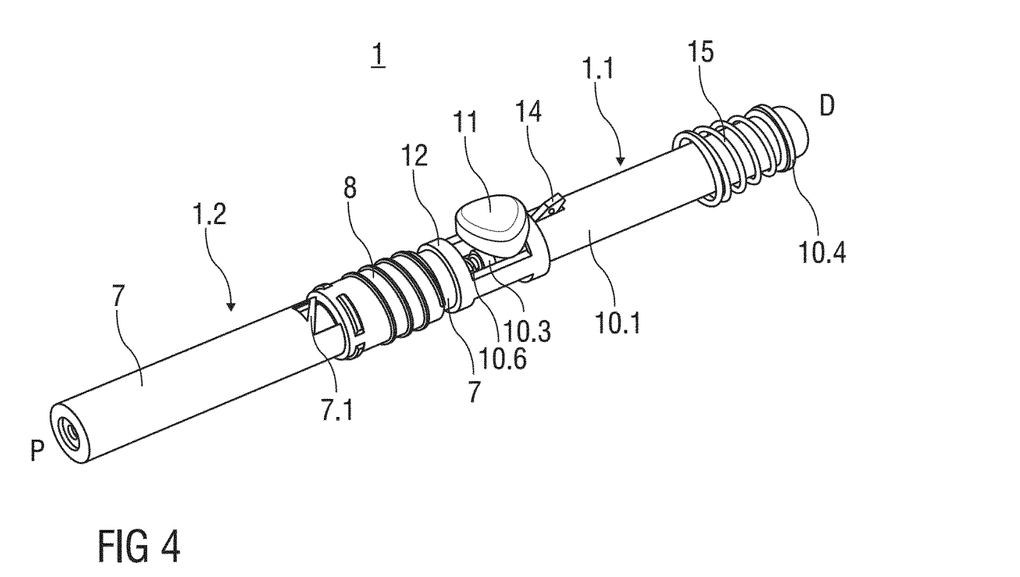
FIG. 4 is an isometric view of the interior of the auto-injector.
Figure 5:
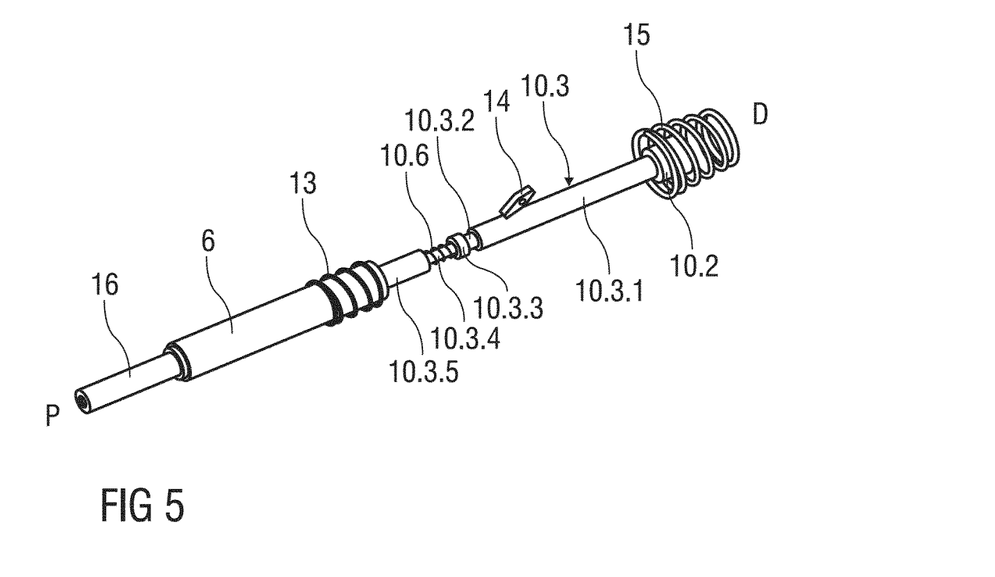
FIG. 5 is another isometric view of the interior of the auto-injector.
Figure 6:
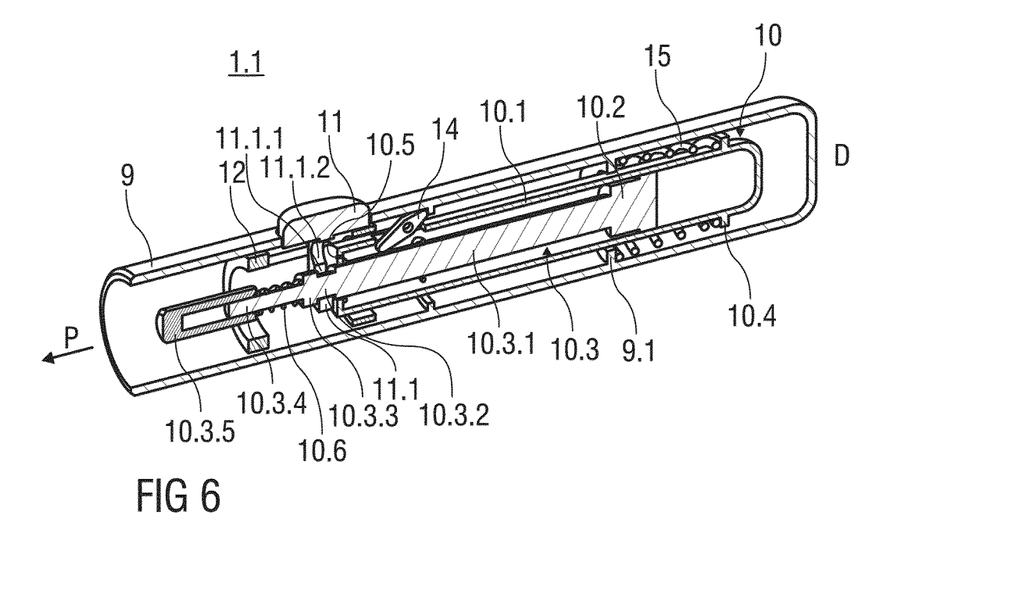
FIG. 6 is a longitudinal section of a reusable engine.

A sequence of operation of the auto-injector 1 is as follows:

The user assembles the packaged syringe 1.2 to a proximal end of the reusable engine 1.1. The connection may be a screw connection as illustrated. Alternative embodiments may involve bayonet connections etc. The assembled auto-injector 1 is shown in FIGS. 1*a*, 1*b* and 3.

Figure 2:
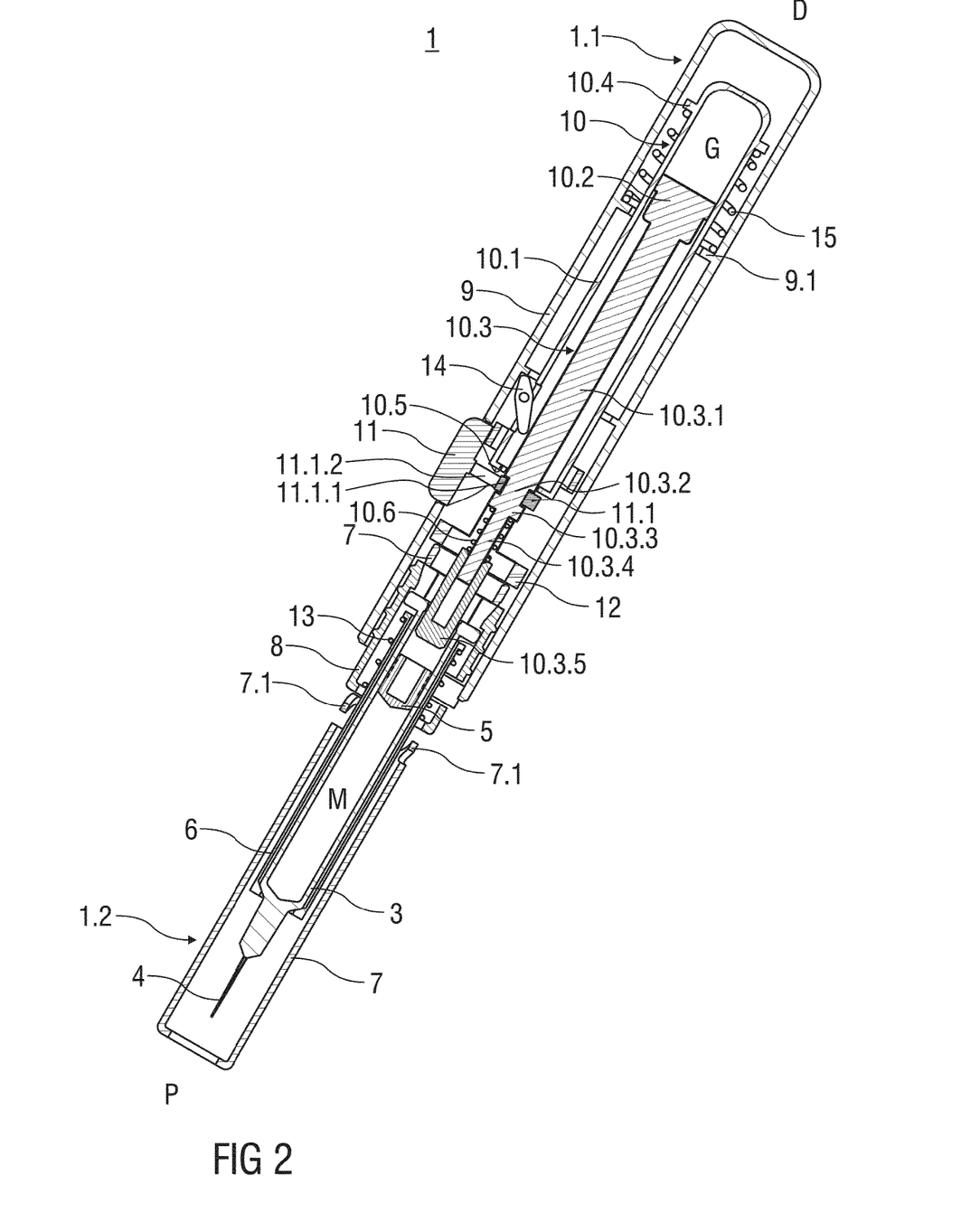
FIG. 2 is a longitudinal section of the auto-injector after removal of a cap and a protective needle sheath.

Then the user removes the cap 2 thereby also removing a protective needle sheath 16 arranged on the needle 4. This situation is illustrated in FIG. 2.

The user places the proximal end P of the auto-injector 1, i.e. the transfer sleeve 7 against an injection site, e.g. a patient's skin. As the auto-injector 1 is pushed against the injection site, the transfer sleeve 7 translates by a small distance in distal direction D against the bias of at least one resilient member 7.1 and displaces the button latch 12 along the longitudinal axis of the auto-injector 1 from the locking position into the unlocked position. This removes the obstruction preventing depression of the trigger button 11. The button latch 12 may be biased in the locking position by a bias spring (not illustrated). Another bias spring may be provided for biasing the trigger button 11 outwardly (not illustrated).

The user depresses the trigger button 11 to commence an injection cycle. As the trigger button 11 is depressed, the dog 11.1 preventing movement of the plunger 10.3 is disengaged. The piston 10.2 and plunger 10.3 start to move in proximal direction P due to the force of the compressed gas G in the cavity.

As the plunger 10.3 moves through the cylinder 10.1, gas, e.g. air on a proximal, low-pressure side of the piston 10.2 is displaced and vented into the atmosphere. The valve 10.5 is arranged to restrict the venting thereby introducing a speed dependent force, hence a damping opposing the plunger 10.3 motion. The valve 10.5 is defined to ensure a damping rate greater than a damping force generated due to friction between the stopper 5 and the inner wall of the syringe 3 and due to hydraulic resistance of the liquid medicament M forced through the small fluid channel in the hollow needle 4. The force on the piston 10.2 from the compressed gas G is always distributed between this damping force and any load applied to the proximal end of the plunger 10.3.

Upon contact with the stopper 5, the plunger 10.3 applies a force to the stopper 5. A syringe spring 13 arranged in the packaged syringe 1.2, the syringe spring 13 arranged to bias the syringe 3 in distal direction with respect to the transfer sleeve 7. The force from the plunger 10.3 is transferred to the syringe spring 13 since a friction force generated by the friction between the stopper 5 and the inner wall of the syringe 3 and by the hydraulic resistance of the liquid medicament M forced through the small fluid channel in the hollow needle 4 is greater than the force of the syringe spring 13 and the force required to insert the needle 4 into the injection site. Thus, the syringe spring 13 is compressed and the needle 4 is inserted into the injection site. An injection depth is controlled by the design of the packaged syringe 1.2, i.e. by the distance, the syringe 3 and support sleeve 6 can travel forwardly before the syringe spring 13 is fully compressed.

In alternative embodiments the injection depth may be controlled by a depth stop within the reusable engine, or within the packaged syringe.

The force applied to the stopper 5 by the plunger 10.3 increases until the friction opposing motion of the stopper 5 within the syringe 3 is overcome. As this force increases, the plunger spring 10.6 will become partially compressed. Once the friction force is exceeded, the stopper 5 starts to move and the medicament M is displaced from the syringe 3 through the needle 4 into the injection site.

When the stopper 5 reaches the end of travel, i.e. the syringe 3 is fully emptied, the gas spring 10 continues to move the plunger 10.3. This additional motion is accommodated by the plunger spring 10.6. The plunger spring 10.6 is defined to generate a force greater than the hydraulic force of emptying the syringe yet weaker than the force of the gas spring 10.

At full extension of the gas spring 10, the piston 10.2 triggers the latch 14 that disengages the cylinder 10.1 from the case 9. If a flexible diaphragm is provided in the cylinder 10.1 under the latch, the piston 10.2 would operate the latch 14 through the diaphragm to decouple the gas spring 10 from the case 9. The cylinder 10.1 then translates in distal direction D under the force of the cylinder spring 15. Since the gas spring 10 has reached its full extension, the plunger 10.3 is withdrawn together with the cylinder 10.1. This removes the force from the stopper 5 allowing the syringe spring 13 to retract the syringe 3 and the needle 4, whereby the needle 4 is extracted from the injection site and gets hidden inside the transfer sleeve 7.

The user may now remove the packaged syringe 1.2 from the reusable engine 1.1. The reusable engine 1.1 may be reset using a tool or a base station (not illustrated). When resetting, the cylinder 10.1 has to be translated in proximal direction P and reengaged to the case 9 by the latch 14. The latch 14 may be biased to return to its position locking the cylinder 10.1 to the case 9. The gas spring 10 has to be recharged by pushing the plunger 10.3 and the piston 10.2 in distal direction D. The cylinder valve 10.5 is a one way valve. Hence, it exerts a minimal force when intaking air into the low pressure side of the cylinder 10.1 when resetting the reusable engine 1.1.

The reusable engine 1.1 may be combined with other types of packaged syringes 1.2.

An arrangement for avoiding wet injection may be optionally provided, i.e. the liquid medicament is not leaking out of the hollow needle 4 before or during needle insertion. This may be achieved by a component which couples the plunger 10.3 to the syringe 3 during needle insertion so the stopper 5 is not pushed. When the injection depth has been reached the plunger 10.3 is decoupled from the syringe 3 and coupled to the stopper 5 to inject the medicament M.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

The invention claimed is:

1. An engine for an auto-injector for administering a dose of a liquid medicament, the engine comprising:
   a case having a distal end and a proximal end arranged to be attached to a packaged syringe containing a syringe with a hollow needle and a stopper for sealing the syringe and displacing the medicament, wherein the syringe is slidably arranged with respect to the case, the case containing
   a drive arranged to, upon activation, push the needle from a covered position into an exposed position, and operate the syringe to supply the dose of medicament, and
   a trigger arranged to lock the drive in a loaded state prior to manual operation and, upon manual operation, to release the drive for injection,
   wherein the drive is arranged as a gas spring comprising a cylinder and a piston with a plunger for transmitting a force of the gas spring, wherein a compressed gas is provided in a high pressure cavity defined between the piston and a distal end of the cylinder, wherein the cylinder is slidably arranged in the case, and wherein a latch is arranged to inhibit translation between the cylinder and the case and to be disengaged by the gas spring in a released state being at least nearly fully extended thus allowing the gas spring in an extended state to be translated in a distal direction.

2. The engine according to claim 1, further comprising a cylinder spring arranged in the case for biasing the cylinder against the case in the distal direction.

3. The engine according to claim 1, wherein the compressed gas is Nitrogen.

4. The engine according to claim 1, wherein the compressed gas exhibits a pressure of approximately 10 bar when the gas spring is in the loaded state.

5. The engine according to claim 1, wherein the trigger is arranged as a trigger button laterally arranged at the case, the trigger button having a dog for engaging the plunger prior to manual operation to inhibit translation of the plunger, wherein the dog is arranged to disengage from the plunger upon manual operation.

6. The engine according to claim 5, wherein the dog is shaped as a loop with an aperture for the plunger, wherein the aperture comprises a narrow portion aligned with the plunger prior to manual operation of the trigger button and a wide portion aligned with the plunger upon manual operation, wherein the plunger has a main section and a locking section, the main section being hidden in the cylinder and the locking section outside the cylinder when the gas spring is in the loaded state, wherein the narrow portion has a diameter smaller than a diameter of the main section but wider than a diameter of the locking section, wherein the wide portion has a diameter at least as wide as the diameter of the main section, wherein the locking section is engaged with the narrow portion prior to manual operation.

7. The engine according to claim 6, wherein beyond the locking section in a proximal direction the plunger comprises a shoulder followed by a pin with the shoulder having a greater diameter than the pin, wherein a plunger front part is telescoped with the pin, wherein a plunger spring is arranged on the pin to bias the plunger front part against the pin.

8. The engine according to claim 5, wherein a second latch is arranged in the case, the second latch slidable between a locking position obstructing the trigger button to inhibit the trigger button from being pressed and an unlocked position allowing the trigger button to be pressed inwardly.

9. The engine according to claim 8, wherein the second latch is arranged to be pushed into the unlocked position by a transfer sleeve arranged in the packaged syringe when a proximal end of the transfer sleeve is pushed against an injection site.

10. The engine according to claim 1, further comprising a valve arranged in the cylinder to restrict venting of a low pressure side of the piston opposite the high pressure cavity.

11. The engine according to claim 10, wherein the valve is arranged to maintain a damping rate greater than a damping force generated due to friction between the stopper and an inner wall of the syringe and due to hydraulic resistance of the liquid medicament forced through the hollow needle.

12. An auto-injector for administering a dose of a liquid medicament, the auto-injector comprising:

a packaged syringe comprising a syringe with a hollow injection needle and a stopper for sealing the syringe and displacing the liquid medicament; and an engine comprising
a case having a distal end and a proximal end arranged to be attached to the packaged syringe, wherein the syringe of the packaged syringe is slidably arranged with respect to the case, the case containing
a drive arranged, upon activation, to push the needle from a covered position into an exposed position, and to operate the syringe to supply the dose of medicament, and
a trigger arranged to lock the drive in a loaded state prior to manual operation and, upon manual operation, to release the drive for injection,
wherein the drive is arranged as a gas spring comprising a cylinder and a piston with a plunger for transmitting a force of the gas spring,
wherein a compressed gas is provided in a high pressure cavity defined between the piston and a distal end of the cylinder,
wherein the cylinder is slidably arranged in the case,
wherein a latch is arranged to inhibit translation between the cylinder and the case and to be disengaged by the gas spring in a released state being at least nearly fully extended thus allowing the gas spring in an extended state to be translated in a distal direction,
wherein the syringe is at least partially arranged inside a tubular syringe retainer arranged for connecting the packaged syringe to the engine and for restricting longitudinal motion of the syringe,
wherein the syringe and the needle are hidden inside the packaged syringe when the drive is in the loaded state,
wherein the syringe is biased in the distal direction by a syringe spring and movable in a proximal direction by the drive into a position with the needle protruding beyond a proximal end of the packaged syringe.

13. The auto-injector according to claim 12, further comprising a tubular transfer sleeve arranged around the syringe to hide the syringe when the drive is in the loaded state, the transfer sleeve biased in the proximal direction and movable in the distal direction when pressed against an injection site, wherein the transfer sleeve extends through the syringe retainer to engage a second latch of the engine.

14. The auto-injector according to claim 12, further comprising a removable cap arrangeable on the packaged syringe.

15. The auto-injector according to claim 14, wherein the cap is arranged to engage a protective needle sheath arrangeable on the needle to remove the protective needle sheath upon removal of the cap.

16. The auto-injector according to claim 12, wherein the trigger is arranged as a trigger button laterally arranged at the case, the trigger button having a dog for engaging the plunger prior to manual operation to inhibit translation of the plunger, wherein the dog is arranged to disengage from the plunger upon manual operation.

17. The auto-injector according to claim 16, wherein the dog is shaped as a loop with an aperture for the plunger, wherein the aperture comprises a narrow portion aligned with the plunger prior to manual operation of the trigger button and a wide portion aligned with the plunger upon manual operation, wherein the plunger has a main section and a locking section, the main section being hidden in the cylinder and the locking section outside the cylinder when the gas spring is in the loaded state, wherein the narrow portion has a diameter smaller than a diameter of the main section but wider than a diameter of the locking section, wherein the wide portion has a diameter at least as wide as the diameter of the main section, wherein the locking section is engaged with the narrow portion prior to manual operation.

18. The auto-injector according to claim 17, wherein beyond the locking section in a proximal direction the plunger comprises a shoulder followed by a pin with the shoulder having a greater diameter than the pin, wherein a plunger front part is telescoped with the pin, wherein a plunger spring is arranged on the pin to bias the plunger front part against the pin.

19. The auto-injector according to claim 16, wherein a second latch is arranged in the case, the second latch slidable between a locking position obstructing the trigger button to inhibit the trigger button from being pressed and an unlocked position allowing the trigger button to be pressed inwardly.

20. The auto-injector according to claim 19, wherein the second latch is arranged to be pushed into the unlocked position by a transfer sleeve arranged in the packaged syringe when a proximal end of the transfer sleeve is pushed against an injection site.

* * * * *